United States Patent [19]

Matyas et al.

[11] 4,415,431

[45] Nov. 15, 1983

[54] INTEGRATED OXYGASIFICATION AND HYDROPYROLYSIS PROCESS FOR PRODUCING LIQUID AND GASEOUS HYDROCARBONS

[75] Inventors: Richard S. Matyas, Broken Arrow; John A. Hamshar, Owasso, both of Okla.

[73] Assignee: Cities Service Company, Tulsa, Okla.

[21] Appl. No.: 397,956

[22] Filed: Jul. 14, 1982

[51] Int. Cl.³ .............................................. C10G 1/00
[52] U.S. Cl. .................................. 208/8 R; 48/197 R
[58] Field of Search ...................... 208/8 R; 48/197 R

[56] References Cited

U.S. PATENT DOCUMENTS

| | | | |
|---|---|---|---|
| 3,782,913 | 1/1974 | Donath | 48/210 |
| 3,960,700 | 6/1976 | Rosen et al. | 208/8 R |
| 3,988,237 | 10/1976 | Davis et al. | 208/8 R |
| 4,162,959 | 7/1979 | Duraiswamy | 208/8 R |
| 4,278,446 | 7/1981 | von Rosenberg et al. | 48/197 R |

Primary Examiner—Delbert E. Gantz
Assistant Examiner—Anthony McFarlane
Attorney, Agent, or Firm—George L. Rushton; Robert H. Sproule; John W. Carpenter

[57] ABSTRACT

Oxygen and steam are mixed with partially reacted carbonaceous material within a first stage gasification zone to produce synthesis gas. The hot synthesis gas long with additional carbonaceous material is then reacted in a second stage hydropyrolysis zone. The reaction mixture is rapidly quenched and removed from the second stage thereby limiting the total second stage high temperature exposure time from about two milliseconds to about two seconds. The resultant products comprise char, gaseous and liquid hydrocarbons including high yields of benzene, toluene and xylene, and $C_1$–$C_4$ gases. The first and second stages may consist of two separate reactors or two reactors integrated into a single vessel, each utilizing either an upflow or downflow configuration.

10 Claims, 2 Drawing Figures

INTEGRATED OXYGASIFICATION AND HYDROPYROLYSIS PROCESS FOR PRODUCING LIQUID AND GASEOUS HYDROCARBONS

BACKGROUND OF THE INVENTION

This invention relates to the reaction of carbonaceous material to produce liquid and gaseous hydrocarbons. More particularly, the invention relates to a two stage process for the hydropyrolysis of carbonaceous material to produce gaseous and liquid hydrocarbons including benzene, toluene and xylene.

It is generally well known that carbonaceous material such as coal is converted to liquid and gaseous hydrocarbons when reacted with hydrogen in the presence of high temperature. Common reactors include the fluidized bed reactor which utilizes a vertical upward flow of reactant gases at a sufficient velocity to overcome the gravitational forces on the carbonaceous particles thereby causing movement of the particles in a gaseous suspension. The fluidized bed reactor is characterized by larger volumes of particles accompanied by longer high temperature exposure times to obtain conversion into liquid and gaseous hydrocarbons.

Another common reactor is the entrained flow reactor which utilizes a high velocity stream of reactant gases to impinge upon and carry the carbonaceous particles through the reactor vessel. Entrained flow reactors are characterized by smaller volumes of particles and shorter exposure times to the high temperature gases.

The two stage entrained flow reactor utilizes a first stage to react carbonaceous char with a gaseous stream of oxygen and steam to produce hydrogen, oxides of carbon, and water. These products continue into the second stage where additional carbonaceous material is fed into the stream. The feed reacts with the first stage stream to produce liquid and gaseous hydrocarbons including large amounts of methane gas and char. The movement of the gases between the first and second stages may be by gravity as in a downflow reactor, or by an inertial propelling force as in an upflow reactor.

Prior two-stage gasification processes have been limited primarily to the production of methane and synthesis gas which then must be upgraded for further use. The second-stage products of prior processes include methane carbon monoxide, carbon dioxide, water, hydrogen and ash. The further upgrading that is required is a shift reaction ($CO + H_2O = CO_2 + H_2$) which generates hydrogen; this additional hydrogen is necessary for the methanation reaction ($CO + 3H_2 = CH_4 + H_2O$). In prior processes, a substantial amount of the methane was made in the further upgrading processes.

In addition, the relatively longer exposure times of the carbonaceous material to the high temperatures caused the rapid devolatilization of the particles into various aromatic compounds, followed by the degradation of the aromatics into smaller straight chain or aliphatic compounds and coke. It is believed, however, that by limiting the high temperature exposure time of the carbonaceous particles, the breakdown of the aromatics into smaller aliphatic compounds and coke is inhibited. The resulting product contains significant amounts of benzene, toluene, and xylene, and other light (low boiling) and heavy (high boiling) aromatics and aliphatic hydrocarbon mixtures including methane gas. The advantage of obtaining liquid hydrocarbons including benzene, toluene and xylene is their use as chemical and petroleum feedstocks. The high industry demand for these feedstocks coupled with their low availability, render them a valuable end product.

Prior art two stage processes for the gasification of coal to produce primarily gaseous hydrocarbons include U.S. Pat. Nos. 4,278,445 by Stickler, 4,278,446 by Von Rosenberg, Jr. and 3,844,733 by Donath. Donath describes a process for two-stage downflow gasification of coal to produce methane rich gas. In the first stage, partially reacted recycle char is reacted with steam and oxygen to produce a first stage synthesis gas including hydrogen and oxides of carbon. In the second stage, the synthesis gas is reacted with coal and steam to produce a methane rich gas (after further upgrading) and partially gasified coal char. The Von Rosenberg and Stickler patents utilize a two stage gasification process distinguished by the high velocity flow of gases through the second stage combined with rapid changes in the acceleration of the gases and entrained coal. The high speed accelerations and decelerations increase the rate of mixing and heat transfer with the carbonaceous feed resulting in the high yields of methane gas.

U.S. Pat. No. 3,960,700 by Rosen describes a process for exposing coal to high heat for short periods of time to maximize the production of desirable liquid hydrocarbons and to reduce the gaseous and polymerized products. The Rosen patent describes a process whereby hydrogen obtained from a separate commercial source is mixed with coal inside a heated reactor. The advantages of utilizing the integrated oxygasification and hydropyrolysis process over the Rosen Process are the reduced complexity and improved thermal efficiency. Process complexity is reduced as follows:

(a) Gas cleanup and treatment operates on only one stream, compared to two or three different streams when the oxygasifier and hydropyrolysis reactor operate apart from each other;

(b) The need to recycle and generate and purify hydrogen is eliminated by feeding raw synthesis gas to the hydropyrolysis reactor;

(c) Oxygen consumption in the hydropyrolysis reactor is reduced or eliminated;

(d) Hydrogen (reaction gas) preheater upstream of hydropyrolysis reactor is eliminated;

(e) Cryogenic gas separation is eliminated and replaced by shift and methanation to pipeline gas.

Thermal efficiency in the integrated process is improved as follows:

(a) Heat available at the oxygasifier outlet is used to heat the hydropyrolysis reactants;

(b) Use of indirect heat transfer is reduced in favor of more efficient direct transport of heat;

(c) Compression and fuel costs associated with hydrogen purification and recycle are eliminated.

Clearly, therefore, there is a need for a hydropyrolysis process utilizing both a relatively inexpensive source of hydrogen and heat, and a short second stage high temperature exposure time to produce an end product containing significant amounts of liquid and gaseous hydrocarbons.

SUMMARY OF THE INVENTION

It is an object of this invention to convert carbonaceous material to gaseous and liquid hydrocarbons utilizing a two stage hydropyrolysis process.

More particularly, it is an object of this invention to convert the carbonaceous material to gaseous and liquid hydrocarbons, including significant amounts of liquid hydrocarbons such as benzene, toluene and xylene, utilizing first stage oxygasification of carbonaceous char as a source of hydrogen and heat for second stage hydropyrolysis of carbonaceous material in which there is a very short second stage high temperature exposure time.

It is another object of this invention to change the temperature, pressure, and second-stage high-temperature exposure time to vary the liquid and gaseous product slate.

It is another object of this invention to carry out the first and second stage reactions in separate reactors or in a single vessel containing both the first and second stages.

It is yet another object of this invention to arrange the reactor or reactors in such a manner that the axial flow of reactor products through the reactor may be in any desired direction.

In accordance with the present invention there is provided a two-stage process for producing liquid and gaseous hydrocarbons from carbonaceous materials. Broadly, oxygen and steam are reacted with partially gasified coal char in the first-stage gasification zone to obtain products including CO, $CO_2$, $H_2$ and $H_2O$. The first-stage products are moved to a second-stage hydropyrolysis zone where the hydrogen reacts with carbonaceous feed material. The second-stage temperature ranges from about 1000° F. to about 3500° F., and the second-stage pressure ranges from about 250 psia to about 5000 psia. The second-stage reactor products are then rapidly cooled such that the total high-temperature exposure time is from about two milliseconds to about two seconds. The rapid quench results in a second-stage product slate of gaseous and liquid hydrocarbons including benzene, toluene, and xylene.

In accordance with the present invention the first and second stages may comprise either two separate reactors or a single vessel containing both the first and second stages similar in concept to the BCR Bigas reactor. The direction of flow of the products through the reactors or vessel is dependent only upon the longitudinal axial alignment of the reactors or single reactor vessel. By utilizing high velocity flows to propel the reactor products through the reactors, the direction of axial alignment of the reactors or vessel may be varied.

DETAILED DESCRIPTION OF THE INVENTION

Figure 1:
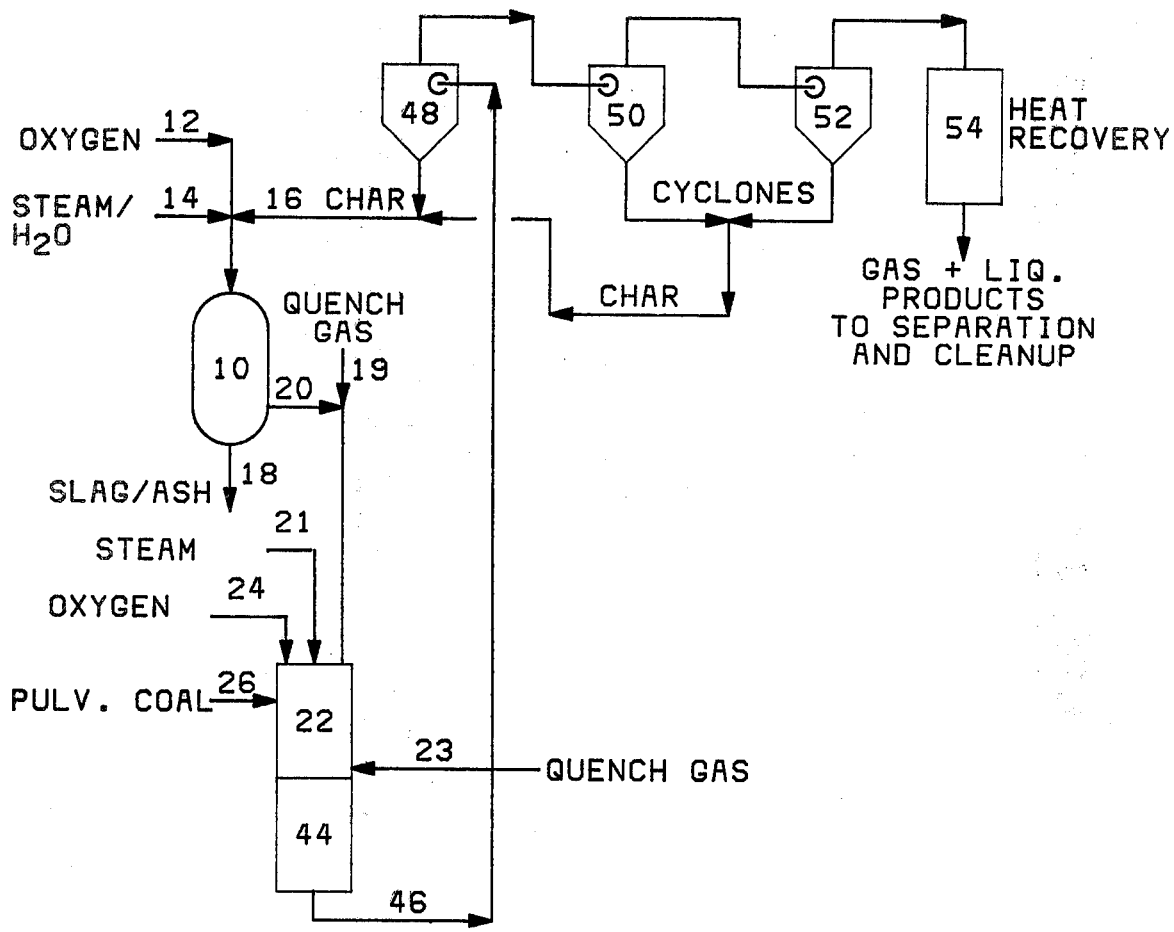
FIG. 1 is a flow diagram showing the two stage process utilizing two downflow reactors.
Figure 2:
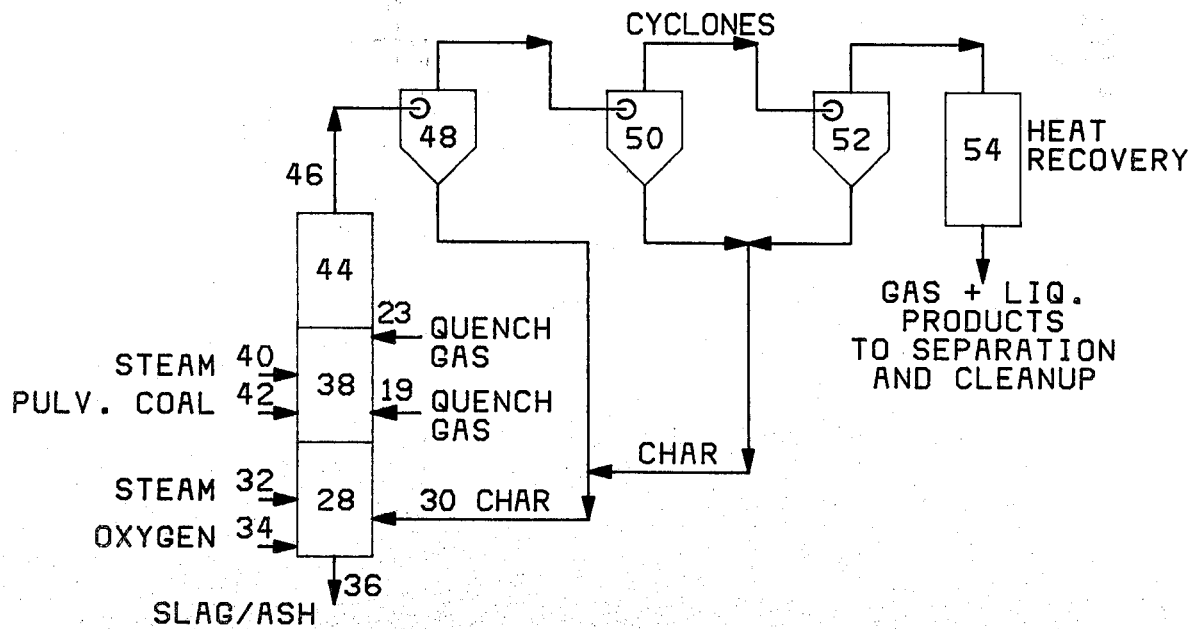
FIG. 2 is a flow diagram showing the two stage process utilizing a single upflow reactor.

The invention comprises a two stage process for the hydropyrolysis of any solid or liquid carbonaceous material, in particular coal. The two stages of the process may occur in separate reactors, or the separate stages may be integrated into a single reactor. The direction of product flow through the stages is not critical; however, an upflow or downflow direction is the most commonly used. For example purposes, FIGS. 1 and 2 illustrate a two reactor downflow process and a one reactor upflow process respectively. Referring first to the two unit downflow process depicted in FIG. 1, oxygen and steam are introduced into the inlet end of a first-stage oxygasifier 10 through conduits 12 and 14 respectively. A partially reacted char is introduced into the inlet end of reactor 10 through conduit 16. Oxygen is introduced on an as-needed basis to maintain the desired operating temperature range in the first stage. Sufficient steam is added to the first stage to insure an adequate supply of hydrogen for the second-stage hydropyrolysis process; steam requirements are therefore dependent upon the second-stage carbonaceous material feed rate, the type of carbonaceous feed introduced, and the operating conditions in the second stage. Higher temperatures and longer high temperature exposure times in the second stage create a need for greater amounts of hydrogen in the second stage. In order to meet second stage hydrogen requirements, 0.01 to 0.03 lbs. of $H_2$ per one lb. of carbonaceous material is required to be fed into the second stage. Further hydrogen requirements in the second stage are met by the reaction of CO and $H_2O$ in the second stage reactor. Gasifier 10 may comprise any pressurized oxygasifier capable of producing synthesis gas ($H_2$, CO). However, an entrained flow or fluidized bed gasifier such as the Texaco and the Mountain Fuels Resources coal gasifiers utilizing down entrained flow, the Saarberg-Otto Process utilizing up entrained flow, or the Westinghouse coal gasifier utilizing upflow pressurized, fluidized bed are preferred. The operating conditions and the desired product slate will determine which type of gasifier is used. A pressurized fluidized bed reactor favors the production of methane, while an entrained flow reactor results in lower costs and higher operating temperatures. In order to ensure consistent feeding, feed pressure in conduits 12, 14 and 16 is 50 to 90 psi above reactor 10 pressure when introducing solid feed materials, and 20 to 50 psi above reactor 10 pressure when introducing liquid and gaseous feed materials. The oxygen and steam react with the partially gasified char at a first-stage reactor pressure from about 250 to 5000 psia, preferably from about 500 psia to about 2000 psia, and a first-stage reactor temperature from about 1500° F. to about 3500° F. preferably from about 1700° F. to about 2500° F., resulting in the production of a first-stage product slate including hydrogen, oxides of carbon, water, and methane gas, along with small amounts of ammonia and hydrogen sulfide. The total residence time of the partially reacted char in the first stage is from about 0.5 to about 15 seconds when using an entrained flow first-stage reactor and from about 10 minutes to about 40 minutes when using a fluidized bed first-stage reactor. Slag and ash are removed from the bottom of reactor 10 through conduit 18. The first-stage production of synthesis gas is exothermic, raising the temperature of the synthesis gas to about 1700° F. to about 3000° F.

The first-stage product slate departs reactor 10 moving downwardly through conduit 20 into the inlet end of the second-stage reactor or hydropyrolyzer 22 which operates at a pressure from about 250 psia to about 5000 psia, preferably from about 500 psia to about 2000 psia, and a temperature from about 1000° F. to about 2000° F., preferably from about 1200° F. to about 1800° F. As necessary to maintain the required reaction temperature inside the second stage, the steam and oxygen may be introduced into the inlet end of reactor 22 through conduits 21 and 24 respectively at a pressure from about 25 psi to about 50 psi above reactor 22 pressure. Excess steam is introduced into reactor 22 to prevent the agglomeration or lay down of carbon on the inside of reactor 22 walls and to prevent local hot spots due to oxygen injection. Reactor 22 may comprise any short residence entrained flow reactor; a preferred reactor is an injector impingement reactor based on rocket technology as described in U.S. Pat. No. 4,169,128 hereby incorporated by reference, which insures a high rate of flow of reactor products and therefore a short residence time within reactor 22. Carbonaceous feed material is introduced through conduit 26 into the synthesis gas stream inside reactor 22 at a pressure from about 50 psi to about 90 psi above the operating pressure of reactor 22. The carbonaceous material includes any solid or liquid material containing carbon and hydrogen such as, but not limited to, coal, lignite, peat, wood, oil shale, tar sands, crude oil and certain chemical and petroleum processing wastes, such as refinery vacuum bottoms. A preferred embodiment of the invention uses coal as the feed material with a particle size of about 200 mesh.

The carbonaceous feed material is rapidly heated by the first-stage product stream resulting in its rapid devolatilization and hydropyrolysis. It has been found that the presence of $CO$, $CO_2$, $CH_4$ and $NH_3$ in the second stage does not inhibit the production of benzene, toluene, xylene, and other liquid products in a short-exposure time, high-temperature hydropyrolysis. $CH_4$ and $CO_2$ are merely diluents which have little effect on the second stage reactions. It is known that CO or synthesis gas may be effectively substituted for hydrogen. The concurrent presence of water vapor is required and the net reaction abstracts hydrogen from water to provide some of the hydrogen consumed in the hydrogenation reactions. This concept may be extended to hydropyrolysis processes utilizing a short high temperature exposure time. Hydrogen is indirectly abstracted from water vapor to satisfy a portion of the hydrogen needs in the second stage reactor, while the remaining hydrogen needs are satisfied by the $H_2$ produced in the first stage.

After pyrolysis, the second stage products are rapidly cooled to a temperature below 1000° F., preferably from about 600° F. to about 900° F., by the introduction of a quench gas through conduit 23 or by the flow of the reactants through a recuperator or heat exchanger 44. The quantity of quench gas is determined by its heat capacity or ability to absorb the sensible heat of the reactor outlet gases. Generally the second stage requires one-half mole of cool recycle quench gas per one mole of reactor outlet gas. The quench gas may comprise any gases or liquids that can be blended rapidly and in sufficient quantity to the reactant mixture in order to readily cool the mixture below the effective reacting temperature. Hydrogen is the preferred quench material, although other products may be used such as those listed in U.S. Pat. No. 3,960,700 which is hereby incorporated by reference. Quench gas may also be introduced through conduit 19 to cool the products exiting the first stage prior to their introduction into the second stage. The total high temperature exposure time of the reactant mixture in the second-stage may vary from about 2 milliseconds to about 2 seconds. The preferable second stage high temperature exposure time is from about 100 milliseconds to about 2 seconds. The total high temperature exposure time, hereinafter referred to as second-stage exposure time, is defined as that time required to heat up, react, and cool the second stage mixture below its effective reacting temperature. The cooling down or quenching of the reactant gases may occur within reactor 22 or subsequent to their departure from reactor 22. For example, if a recuperator or heat exchanger 44 is used, the final quenching of the reactant mixture will not occur until the second-stage products are within recuperator 44.

The second-stage product slate includes: benzene, toluene and xylene, from about ½% carbon conversion to about 20% carbon conversion. Carbon conversion is defined as the weight ratio expressed as a percentage, of the carbon found in the second-stage end products to the total amount of carbon in the second-stage carbonaceous feed material. The second-stage product slate also includes: $C_1$–$C_4$ gases, from about 5% carbon conversion to about 80% carbon conversion, and liquids having a boiling point less than 700° F. (excluding BTX) from about 1% carbon conversion to about 30% carbon conversion.

The short exposure time in the second stage reactor is conducive to the formation of aromatic liquids and light oils. It has been found that rapid heating of carbonaceous materials not only drives out the volatiles from the host particles (devolatilization), but also thermally cracks larger hydrocarbons into smaller volatiles which escape from the host particle so rapidly that condensate reactions are largely bypassed. With a rapid hydrogen quench, these volatiles are stabilized and condensation and further cracking reactions are inhibited. The stabilization occurs either by reaction with hydrogen to form a less reactive product or by lowering the internal energy of the volatile below its reactive energy level. The net result is the rapid production of volatiles and then a rapid stabilization of these volatiles before they can degrade to low molecular weight gases or polymerize to solids.

Another embodiment of the two-stage process is the upflow single vessel configuration process depicted in FIG. 2. The outlet end of an upflow reactor comprising the first stage is connected directly to the inlet end of a second-stage hydropyrolizer. The two stages can comprise two physically separate compatible reactors utilizing a high product flow rate such as an injector impingement, short-residence time, entrained-flow reactor developed from rocket engine technology, or the two stages may comprise integral parts or stages of one unit similar to the BCR Bigas reactor as described in U.S. Pat. No. 3,746,222 hereby incorporated by reference. The direction of axial alignment of the reactor is not important since high velocity entrained flow is not gravity dependent; rockets and jet aircraft engines perform in any direction to provide the high rate of flow and short exposure time required to achieve the desired product slate. Referring now to FIG. 2, a partially gasified char is introduced into the inlet end of the first-stage reactor 28 through conduit 30. Along with the char, steam and oxygen are introduced through conduits 32 and 34 respectively. Oxygen is introduced on an as needed basis to maintain the desired operating temperature range for both the first and second stage. Sufficient steam is introduced to insure an adequate supply of hydrogen for the second-stage hydropyrolysis reactions. In order to meet second-stage hydrogen requirements, 0.01 to 0.03 lbs. of $H_2$ per one lb. of carbonaceous material is required to be fed into the second stage. Further hydrogen requirements in the second stage are met by the reaction of CO and $H_2O$ in the second-stage reactor. The oxygen and steam react with the char within reactor 28 at a reactor pressure from about 250 psi to about 5000 psi, preferably from about 500 psi to about 2000 psi, and a temperature from about 1500° F. to about 3500° F., preferably from about 1700° F. to about 2500° F., to produce the first stage synthesis gas. Slag and ash empty out the bottom of reactor 28 through conduit 36. The total residence time of the partially reacted char in the first stage is from about 0.5 to about 15 seconds when using an entrained flow reactor system, and from 10 minutes to about 40 minutes when using a fluidized bed reactor system. The synthesis gas is projected upwardly into the second stage hydropyrolyzer 38 at a temperature from about 1700° F. to about 2500° F. Quench gas may be introduced through conduit 19 to cool the synthesis gas mixture to the proper temperature. Steam is introduced into the second stage through conduit 40 in order to provide an additional source of hydrogen needed in the reactions, to moderate reaction temperatures at oxygen injection points and to prevent carbon laydown or agglomeration upon the walls of the reactor. The carbonaceous feed material is then introduced through conduit 42 into the second stage where it reacts with the heated synthesis gas stream, and is then rapidly cooled to a temperature below 1000° F., preferably from about 600° F. to 900° F., by the introduction of a quench gas through conduit 23 or by flow through recuperator 44. The total exposure time of the carbonaceous feed material in the second stage may vary from about two milliseconds to about two seconds, the preferred exposure time varying from about 100 milliseconds to about 2000 milliseconds. The second stage product ranges are the same as previously described for the two reactor downflow process.

Other embodiments of the two stage process are possible utilizing either a single vessel or separate reactors. The direction of product movement through the first and second stages is not limited to either upflow or downflow when a high velocity propelling force is used to overcome gravitational forces and to insure rapid product movement through the reactors.

Referring now to either FIGS. 1 or 2, recuperator or heat exchanger 44 is positioned at the outlet ends of the second-stage reactors 22 (FIG. 1) and 38 (FIG. 2) to rapidly cool the second stage reaction products and recover the heat of reaction from them. The recuperator is a countercurrent heat exchanger designed to recover the sensible heat from the gasifier products as well as to provide a method to rapidly quench the reactant products. The recuperator may consist of two parts, a product quench and a char cooler. The product quench can be used to preheat reactants or make high pressure steam, while the char cooler is primarily used for cooling the hot char. When recuperator 44 is not used, an inlet into the second stage for direct quench may be used.

The reaction products depart recuperator 44 through conduit 46 and enter a cyclone separator 48 where the partially reacted entrained char is separated from the gaseous products and then sent to the first stage reactor for oxygasification. The second stage product gas is further treated in cyclones 50 and 52 for removal of the remaining char. The second stage product gas is then transferred to a heat recovery unit 54 for further cooling. The heat recovery unit 54 comprises a series of heat exchangers that condense liquids and lower the product temperatures to allow for further processing, while at the same time generating medium and low pressure steam. Further separation and clean up of the gaseous and liquid products occurs downstream of heat recovery unit 54.

After cooling, the second stage product slate includes, but is not limited to, benzene, toluene, xylene, and $C_1$-$C_4$ gases. Operating conditions in the second stage gasifier may be regulated to also obtain a product with significant amounts of the following additional products: gasification mode—hydrogen, water, carbon monoxide, carbon dioxide, hydrogen sulfide, and lesser amounts of $-700°$ F. boiling point oil consisting of a mixture of light aromatic and aliphatic hydrocarbons and ammonia; petrochemical mode—hydrogen, water, carbon dioxide, carbon monoxide and $-700°$ F. oil with lesser amounts of hydrogen sulfide and ammonia, C-3 and C-4 hydrocarbons; liquefaction mode—hydrogen, water, carbon monoxide, carbon dioxide, $-700°$ F. oil and $+700°$ F. boiling point oil consisting of a mixture of heavy aromatic and aliphatic hydrocarbons and lesser amounts of ethylene, hydrogen sulfide and ammonia. The product slates are dependent upon coal type, pressure, temperature and second-stage exposure time. Pressure, temperature and second-stage exposure time are operating parameters that can be varied within the reactor system. The gasification mode represents those process conditions for achieving optimum production of methane with some co-production of benzene, toluene, and xylene. The gasification mode represents more severe second-stage operating conditions requiring higher temperatures and pressures, and longer high-temperature exposure times. On the other hand, the liquefaction mode achieves a product slate highest in benzene, toluene, xylene and oils. Second-stage process conditions in the liquefaction mode require very short high temperature exposure times, along with lower temperatures and pressures. The petrochemical mode represents those process conditions for achieving maximum yields of petro-chemicals including benzene, toluene, xylene, light oils, and $C_1$-$C_4$ hydrocarbons Second-stage process conditions require relatively low temperatures, high pressures and exposure times lying between the two extremes of the gasification and liquefaction processes. The following examples illustrate the resulting products when the reactor conditions are varied to achieve the gasification, liquefaction, and petrochemical modes.

EXAMPLE 1 (GASIFICATION MODE)

Partially gasified Kentucky No. 9 bituminous char is added at 59.36 lbs/hour to the first stage of a two unit entrained flow gasifier along with 60.83 lbs/hour of oxygen and 75.00 lbs/hour of steam. The reactants are added simultaneously into the reactor at the following temperatures: char—below 620° F.; oxygen—approximately 250° F.; and steam—approximately 480° F. A first stage product slate will result comprising:

|  | lbs/hour |
|---|---|
| $H_2O$ | 56.94 |
| $CH_4$ | 0.28 |
| CO | 61.56 |
| $CO_2$ | 57.94 |
| $N_2$ | 0.12 |
| $H_2$ | 2.78 |
| $H_2S$ | 0.96 |
| $NH_3$ | 0.72 |

The first-stage product slate, is introduced into the second-stage, short-residence time, entrained-flow reactor at a temperature of approximately 1900° F. Added to the second-stage hydropyrolyzer is 11.40 lbs/hour of $O_2$ and 136.04 lbs/hour of Kentucky No. 9 bituminous MF coal. A second-stage reactor pressure of 1,000 psia and a mixing temperature of approximately 1690° F. is maintained.

The reactor mixture is cooled by the indirect quenching in the recuperator section resulting in a total second-stage exposure time of 1,850 milliseconds. After separation of the char the second-stage products will comprise:

|  | lbs/hour |
|---|---|
| $C_6H_6$ | 11.95 |
| $C_7H_8$ | 0.11 |
| $C_8H_{10}$ | 0.03 |
| $H_2O$ | 29.19 |
| $CH_4$ | 25.54 |
| $CO$ | 103.81 |
| $CO_2$ | 89.56 |
| $C_2H_6$ | 0.39 |
| $H_2S$ | 4.19 |
| $NH_3$ | 0.90 |
| $H_2$ | 4.15 |
| $N_2$ | 1.05 |
| Oil, −700° F. B.P. (not including BTX) | 0.51 |

EXAMPLE 2 (LIQUEFACTION MODE)

Partially gasified Western Kentucky bituminous coal char is added at 54.66 lbs/hour to an entrained flow gasifier along with 49.31 lbs/hour of $O_2$ and 13.40 lbs/hour of steam. The products are added simultaneously at the following temperatures: char—below 620° F.; oxygen—approximately 250° F.; and steam—approximately 480° F. A first stage product slate will comprise:

|  | lbs/hour |
|---|---|
| $H_2O$ | 4.45 |
| $CH_4$ | 0.14 |
| $CO$ | 84.22 |
| $CO_2$ | 13.29 |
| $H_2$ | 1.89 |
| $NH_3$ | 0.52 |
| $H_2S$ | 0.88 |
| $N_2$ | 0.11 |

The first-stage product slate is introduced into the second-stage, short-residence time, entrained-flow reactor at a temperature of approximately 1900° F. Added to the second-stage hydropyrolyzer is 13.01 lbs/hour of $O_2$, 25.48 lbs/hour of steam and 135.70 lbs/hour of Western Kentucky bituminous MF coal. A pressure of approximately 800 psia and a mixing temperature of approximately 1700° F. is maintained in the second-stage hydropyrolyzer.

The reaction mixture is cooled by indirect quenching in the recuperator section resulting in a total second stage exposure time of approximately 150 milliseconds. After separation of the char, the second stage products will comprise:

|  | lbs/hour |
|---|---|
| $C_6H_6$ | 8.48 |
| $C_7H_8$ | 1.28 |
| $C_8H_{10}$ | 1.03 |
| $H_2O$ | 14.38 |
| $CH_4$ | 10.95 |
| $CO$ | 70.98 |
| $CO_2$ | 75.13 |
| $C_2H_4$ | 0.21 |
| $C_2H_6$ | 2.54 |

-continued

|  | lbs/hour |
|---|---|
| Oil, −700° F. BP (not including BTX) | 14.54 |
| Oil, +700° F. BP | 17.44 |
| $H_2$ | 3.38 |
| $NH_3$ | 1.52 |
| $N_2$ | 0.11 |
| $H_2S$ | 3.85 |

EXAMPLE 3 (PETROCHEMICAL MODE)

Partially gasified Alberta Forestburg coal char is added at 59.41 lb/hour to the first stage of a pressurized fluidized-bed reactor along with 40.15 lbs/hour of $O_2$ and 27.44 lbs/hour of steam. Reactants are added simultaneously into the reactor at the following temperatures: char—below 620° F.; oxygen—approximately 250° F.; and steam—approximately 480° F. The first-stage product slate will comprise:

|  | lbs/hr |
|---|---|
| $H_2O$ | 2.63 |
| $CH_4$ | 2.89 |
| $CO$ | 101.04 |
| $CO_2$ | 7.44 |
| $H_2S$ | 0.41 |
| $NH_3$ | 1.05 |
| $H_2$ | 3.56 |
| $N_2$ | 0.21 |

The first-stage product slate is introduced into the second-stage, short-residence time, entrained-flow reactor at a temperature of approximately 1850° F. Steam is added at 32.96 lbs/hour to the second stage along with 144.51 lbs/hour of Alberta Forestburg subbituminous MF coal. A pressure of approximately 2000 psia and a mixing temperature of approximately 1200° F. is maintained in the second stage hydropyrolyzer.

The reaction mixture is quenched by indirect quenching in the recuperator section resulting in a total second stage exposure time of 500 milliseconds. After separation of the char, the second stage reaction products will comprise:

|  | lbs/hour |
|---|---|
| $C_6H_6$ | 12.49 |
| $C_7H_8$, $C_8H_{10}$ | 0.48 |
| $H_2O$ | 20.14 |
| $CH_4$ | 13.74 |
| $CO$ | 89.69 |
| $CO_2$ | 72.09 |
| $C_2H_6$ | 10.04 |
| $C_3H_8$ | 0.53 |
| $C_4H_{10}$ | 0.13 |
| $NH_3$ | 1.86 |
| $N_2$ | 0.21 |
| $H_2S$ | 0.93 |
| Oil, −700° F. BP (not including BTX) | 12.49 |

While the present invention has been described herein with reference to particular embodiments thereof, a latitude of modifications, various changes and substitutions are intended in the foregoing disclosure, and in some instances some features of the invention will be employed without a corresponding use of other features without departing from the scope of the invention as set forth.

We claim:

1. A two-stage process for producing liquid and gaseous hydrocarbons from carbonaceous materials, comprising:
   (a) reacting oxygen and steam with partially gasified carbonaceous char in a first-stage gasification zone to obtain products which primarily include oxides of carbon, hydrogen, and water;
   (b) separating the first-stage gaseous products from solid residue:
   (c) reacting the hot first-stage gaseous products, as the primary heat source and heat transfer medium, with carbonaceous material in a second stage hydropyrolysis zone at a temperature from about 1000° F. to about 3500° F. and a pressure from about 250 psia to about 5000 psia; and
   (d) rapidly cooling the second-stage reaction and products such that the total high temperature exposure time of said products is from about 2 milliseconds to about 2 seconds, to produce gaseous and liquid hydrocarbons.

2. The two-stage process as recited in claim 1 wherein the gaseous and liquid products include:
   (a) benzene, toluene and xylene, from about ½% carbon conversion to about 20% carbon conversion;
   (b) $C_1$–$C_4$ gases, from about 5% carbon conversion to about 80% carbon conversion; and
   (c) liquids having a boiling point less than 700° F., from about 1% carbon conversion to about 30% carbon conversion.

3. The two-stage process as recited in claim 2 wherein:
   (a) the temperature in the second-stage hydropyrolysis zone is from about 1200° F. to about 1800° F.;
   (b) the pressure in the second-stage hydropyrolysis zone is from about 500 psia to about 2000 psia; and
   (c) the second-stage high temperature exposure time is from about 100 milliseconds to about 2 seconds.

4. The two-stage process as recited in claim 2 wherein:
   (a) the temperature in the first-stage gasification zone is from about 1500° F. to about 3500° F.;
   (b) the pressure in the first-stage gasification zone is from about 250 psia to about 5000 psia; and
   (c) the first-stage residence time is:
      (1) from about 0.5 seconds to about 15 seconds when using an entrained-flow reactor,
      (2) from about 10 minutes to about 40 minutes when using a fluidized-bed reactor.

5. The two-stage process as recited in claim 2 additionally comprising:
   (a) moving the first-stage reactants downwardly through the first-stage gasification zone; and
   (b) moving the first-stage gaseous products and carbonaceous material directly in an downwardly through the second-stage hydropyrolysis zone positioned below the outlet end of the first-stage zone.

6. The two-stage process as recited in claim 5 additionally comprising moving the first-stage gaseous reaction products directly between a first reactor comprising the first-stage zone and a second reactor comprising the second-stage zone.

7. The two-stage process as recited in claim 2 additionally comprising:
   (a) moving the first-stage reactants upwardly through the first-stage gasification zone; and
   (b) moving the first-stage gaseous products and the carbonaceous material directly in an upwardly through the second-stage hydropyrolysis zone positioned above the outlet end of the first-stage zone.

8. The two-stage process as recited in claims 5 or 7 additionally comprising moving the first-stage gaseous reaction products directly between a first-stage zone and a second-stage zone integrated within one reactor.

9. A two-stage process as recited in claim 6 additionally comprising:
   (a) separating partially gasified coal char from the second-stage reaction products; and
   (b) injecting the coal char into the first-stage gasification zone.

10. The two-stage process as recited in claim 8 additionally comprising:
    (a) separating partially gasified coal char from the second-stage reaction products, and
    (b) injecting the coal char into the first-stage gasification zone.

* * * * *